United States Patent
Huang

[11] Patent Number: 6,012,468
[45] Date of Patent: Jan. 11, 2000

[54] STRUCTURE OF A TOOTHPICK

[76] Inventor: Shih-Yen Huang, 2 Fl., No. 27, Fwu-Yuh Street, Sanchung, Taipei Hsien, Taiwan

[21] Appl. No.: 09/296,263

[22] Filed: Apr. 22, 1999

[51] Int. Cl.[7] .............................. A61C 15/00; A45D 44/18
[52] U.S. Cl. ........................... 132/321; 132/321; 132/309
[58] Field of Search ..................................... 132/321, 329, 132/309, 73, 76.4; 30/355; 433/142

[56] References Cited

U.S. PATENT DOCUMENTS

| | | | |
|---|---|---|---|
| 1,982,285 | 11/1934 | Bronner | 132/321 |
| 1,997,877 | 4/1935 | Spanel | 132/321 |
| 3,438,486 | 4/1969 | Pinkas | 132/321 |
| 5,044,041 | 9/1991 | Ljungberg | 132/321 |
| 5,775,346 | 7/1998 | Szyszkowski | 132/321 |

*Primary Examiner*—John J. Wilson
*Assistant Examiner*—Robyn Doan
*Attorney, Agent, or Firm*—Jacobson, Price, Holman & Stern, PLLC

[57] ABSTRACT

An improved structure of a toothpick is disclosed, wherein a toothpick rod is integrally made of a flexible plastic material, the tip portions on the two ends of the toothpick rod are formed as flat wedge shapes, two sides or surface of the tip portions are formed with a coarse surface with sawteeth, characterized in that the thickness of the two tip portions of the toothpick are different and the thicker tip portion is formed with a hook on the rear rim thereof. In using the aforementioned toothpick, an user may select required end of the toothpick according to the gap between teeth. The hook on the rear end of the tip portion serves to provide a firmly clamping force as the toothpick serves as a fork for forking foods, such as fruits or cake. Further, by the installation of the hook, the present invention has the function of indication. Thereby, the user may identify which end is thicker so that an user may use the toothpick conveniently.

2 Claims, 2 Drawing Sheets

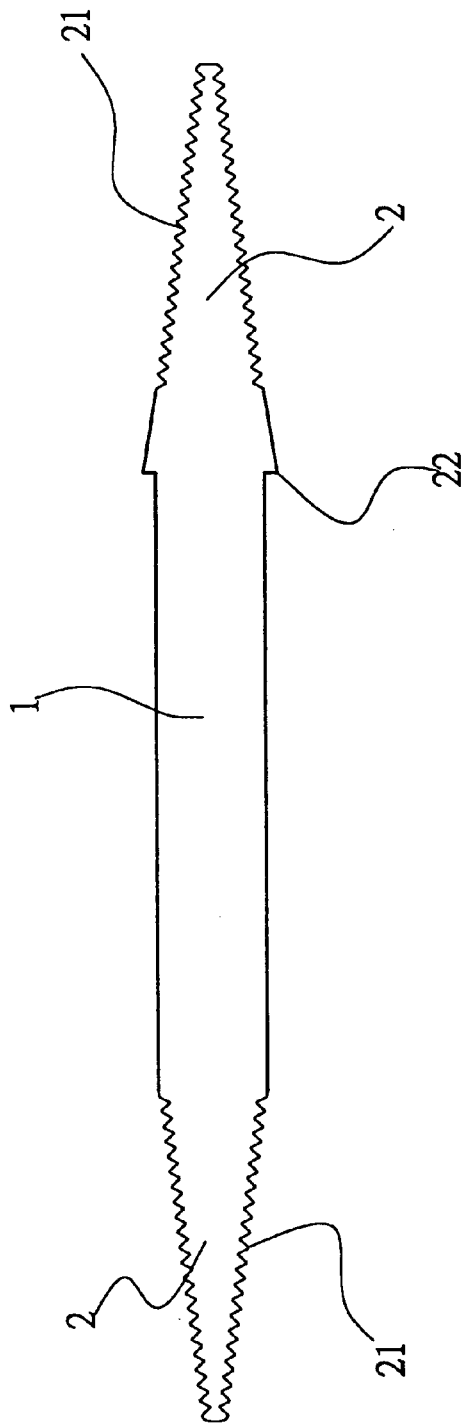
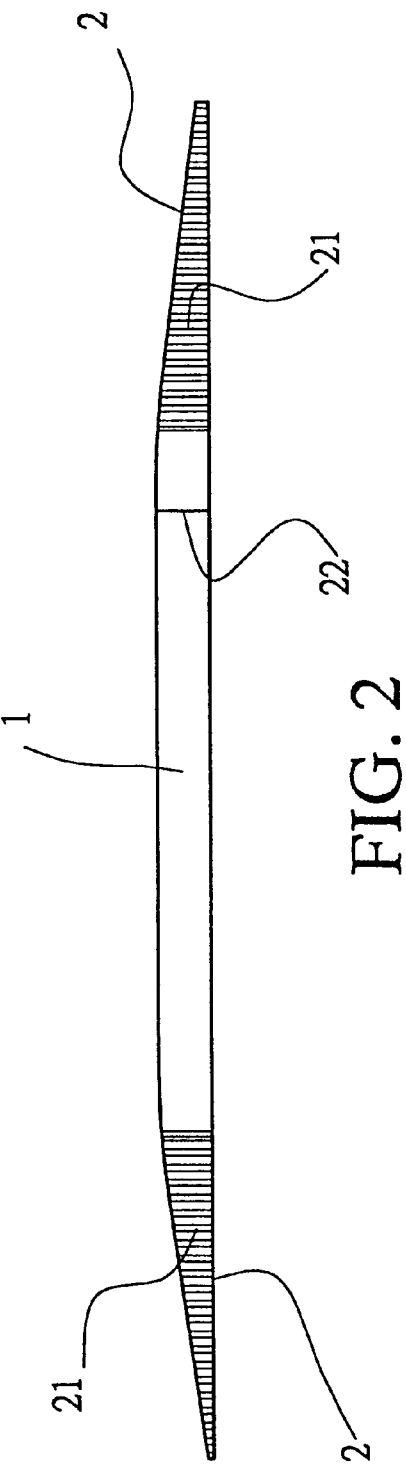

STRUCTURE OF A TOOTHPICK

BACKGROUND OF THE INVENTION

1. Field of the Invention

The present invention relates to an improved structure of a toothpick, and especially to a toothpick with two ends having different thickness, one end of the tip portion of the toothpick has a hook on the rear rim thereof, which can be employed as a fork.

2. Description of the Prior Art

U.S. Pat. Nos. 4,314,574, 4,913,176 and 3,799,256 discloses prior art toothpick designs. A toothpick is made of thin piece. One end of the toothpick is formed with a coarse surface with triangle sawteeth or a plurality of convex portions. The prior art toothpick only has one tip portion with a finite width. Thus, if it is too thin, toothpick is easily broken or difficult to be applied with a force. If it is too thick, although a force is easily applied, when the gap between teeth is too small, the toothpick can not attain the inner part of the gap. Moreover, the coarse surface on the tip portion of the toothpick is formed with triangular sawteeth or convex portions along the inclination of the tip portion. When the toothpick is inserted into the gap between teeth, the toothpick has no sufficient force to pull dregs out.

Moreover, general toothpicks often serve as a fork for forking fruits or cakes. Since a prior art toothpick has a tapered and smooth tip portion, thus it is not sufficient to pick up a fruit or cake conveniently.

SUMMARY OF THE INVENTION

Accordingly, the object of the present invention is to provide an improved structure of a toothpick, the toothpick has two tip ends with different thickness.

Another object of the present invention is to provide an improved structure of a toothpick, a hook is formed at the rear end of the thicker tip end of the toothpick for providing a stronger clamping force to be used as a fork.

Another object of the present invention is to provide an improved structure of a toothpick, a hook is formed at the rear rim of the thicker tip end of the toothpick for identifying the tip ends with different thickness.

Another object of the present invention is to provide an improved structure of a toothpick. In the sawteeth structure on the tip portion, each circular notch are enclosed with acute tip having acute angles on the opening thereof, thus if the toothpick according to the present invention is employed to pick dregs, irrespective of pushing or pulling the toothpick, the dregs can be picked out by the acute tip.

Thus, the present invention provides an improved structure of a toothpick, wherein a toothpick rod is integrally made of a flexible plastic material, the tip portions on the two ends of the toothpick rod are formed as flat wedge shapes, two sides or surface of the tip portions are formed with a coarse surface with sawteeth. Characterized in that the thickness of the two tip portions of the toothpick are different and the thicker tip portion is formed with a hook on the rear edge thereof. The sawteeth structure is formed by a plurality of circular notches with a peripheral larger than a semicircular.

Accordingly, in using the present invention, the user may select the required end of toothpick according to the sizes of gaps between teeth. Moreover, the hook on the rear rim of the thicker tip portion has the functions of preventing sliding and of indication so as to be used as a fork. Thus, the user may identity the differences therebetween.

The present invention will be better understood and its numerous objects and advantages will become apparent to those skilled in the art by referencing to the following drawings in which:

BRIEF DESCRIPTION OF THE DRAWINGS

FIG. 1 is a perspective view showing the embodiment of the present invention.

FIG. 2 is a lateral plane view of FIG. 1.

DETAILED DESCRIPTION OF THE PREFERRED EMBODIMENT

Figure 3:
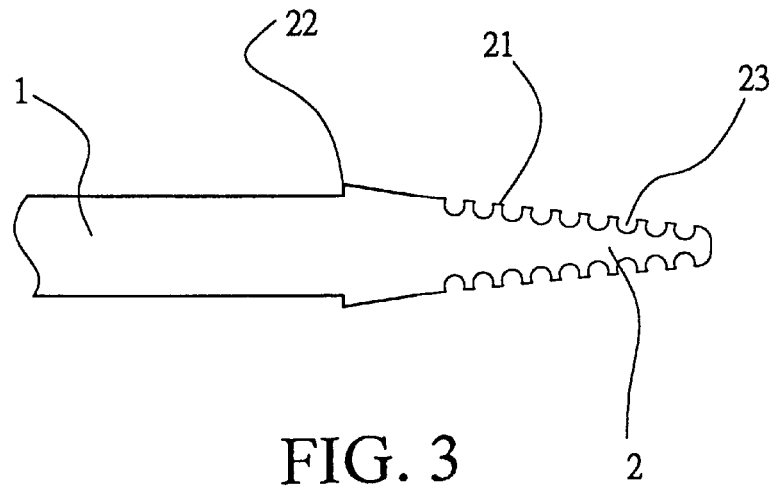
FIG. 3 is a perspective view showing another embodiment of the present invention.

As shown in FIGS. 1 to 3, the improved structure of a toothpick is illustrated. A toothpick rod 1 is integrally made of a plastic material. The tip portions 2 on the two ends of the toothpick rod I are formed as flat wedge shapes. Two sides or surface of the tip portions 2 are formed with sawteeth 21. Characterized in that the thickness of the two tip portions 2 of the toothpick are different and the thicker tip portion 2 is formed with a hook 22 on the rear edge thereof.

The sawteeth structure 21 is formed by a plurality of concave portions 23 (as shown in FIG. 3), thus the user may select the required tip portion 2 according to the gaps between teeth. Moreover, the hook 22 on the rear end of the one tip portion 2 serve to provide a firmly clamping force as the toothpick serves as a fork for forking foods, such as fruits. Further, by the installation of the hook 22, the present invention has the function of indication. Thereby, the user may identify which end is thicker so that an user may use toothpick conveniently.

With reference to FIG. 3, in the aforementioned toothpick structure, since the sawteeth structure 21 is formed by a plurality of circular notches with a peripheral larger than a semicircular. Thus, each circular notch 23 are enclosed with acute tip having acute angles on the opening thereof, thus if the toothpick according to the present invention is employed to pick dregs from the tooth's gaps, irrespective of pushing or pulling the toothpick, the dregs can be picked out by the acute tip. This is superior to the cited reference wherein the acute tip is replaced by triangular tips or convex blocks.

Figure 4:
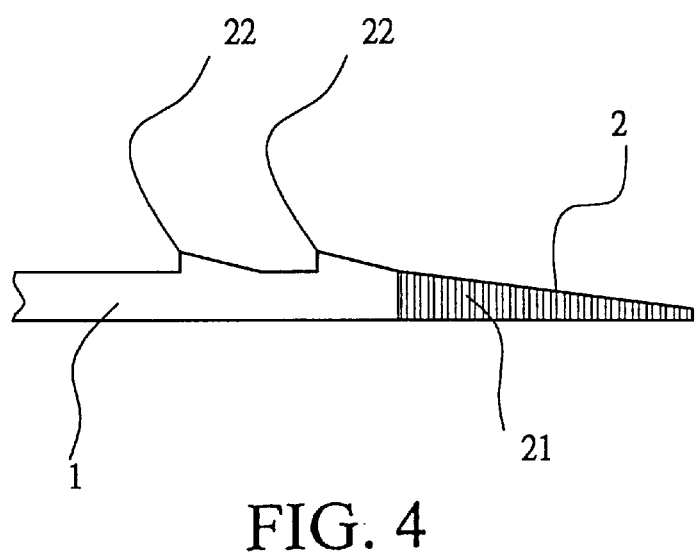
FIG. 4 is a perspective view showing a further embodiment of the present invention.
Figure 5:
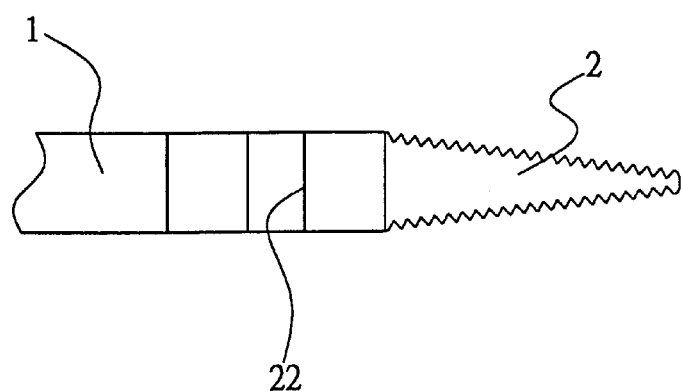
FIG. 5 is a top view of FIG. 4.

Further referring to FIGS. 4 and 5, the original hook 22 at the wider tip portion 2 can be formed on the top of the toothpick 1.

Although the present invention has been described using specified embodiment, the examples are meant to be illustrative and not restrictive. It is clear that many other variations would be possible without departing from the basic approach, demonstrated in the present invention.

What is claimed is:

1. An improved structure of a toothpick, wherein a toothpick rod is integrally made of a flexible plastic material, tip portions on two ends of the toothpick rod are formed as flat wedge shapes, two sides or surface of the tip portions are formed with a coarse surface with sawteeth, characterized in that:

thickness of the two tip portions of the toothpick are different and a thicker tip portion is formed with a hook on the rear rim thereof.

2. The improved structure of a toothpick as claimed in claim 1, wherein the sawteeth structure is formed by a plurality of circular notches with a peripheral larger than a semicircular.

* * * * *